United States Patent [19]

Guillemin et al.

[11] 4,454,749
[45] Jun. 19, 1984

[54] DEVICE FOR COLUMN CHROMATOGRAPHY APPARATUS

[75] Inventors: Claude Guillemin, Paris; Jean Lissot, Brie Comte Robert; Jean-Pierre Vasseur, Longjumeau, all of France

[73] Assignee: Prolabo, Paris, France

[21] Appl. No.: 305,331

[22] Filed: Sep. 24, 1981

[30] Foreign Application Priority Data

Sep. 26, 1980 [FR] France ............................. 80 20987

[51] Int. Cl.³ ............................................. G01N 31/08
[52] U.S. Cl. .................................. 73/23.1; 73/61.1 C; 73/864.81
[58] Field of Search ............. 73/23.1, 61.1 C, 863.71, 73/863.72, 863.73, 864.81, 864.82, 864.83, 864.84, 864.85, 864.86, 864.87; 55/67, 197, 386

[56] References Cited

U.S. PATENT DOCUMENTS

3,119,251  1/1964  Bowers ................................ 73/23.1
3,150,517  9/1964  Kuffer et al. ....................... 73/23.1
3,201,922  8/1965  Villalobos ........................... 73/23.1
3,203,249  8/1965  Jentzsch et al. .................... 73/23.1
3,592,046  7/1971  Cramers et al. .................... 73/23.1
3,675,466  7/1972  Linenberg .......................... 73/23.1

Primary Examiner—Stephen A. Kreitman
Attorney, Agent, or Firm—Burns, Doane, Swecker & Mathis

[57] ABSTRACT

For a fluid chromatography apparatus including a precolumn and an analytical column, a device is provided with means for operably connecting said precolumn and column, said connecting means comprising a body member provided with support surfaces for a column inlet and a precolumn outlet, and said body member including a plurality of passages adapted to independently functionally interconnect said precolumn outlet and said column inlet with each other, and individually independently with fluid inlet and/or outlet means, either internally or externally.

20 Claims, 14 Drawing Figures

DEVICE FOR COLUMN CHROMATOGRAPHY APPARATUS

BACKGROUND OF THE INVENTION

1. Field of the Invention

The present invention relates to device operably connecting a precolumn with an analytical column in a chromatography system, and, more especially in a liquid chromatography system, together with the use of such device in an automatic industrial or laboratory chromatograph.

2. Description of the Prior Art

In chromatography, and in particular in liquid phase chromatography, the analysis of samples containing heavy compounds which are undesirable for the purpose of the analysis, or which must be identified separately, or the analysis of samples that are suspensions or analysis of samples containing highly dilute compounds, require the combination of a precolumn with the analytical column. The precolumn is to effect a preliminary treatment upon the sample prior to its injection in the separation column.

Depending upon the analytical problem in question, the precolumn and the column may be traversed by a fluid, in series or separately from each other.

The precolumn and the column may be flushed in series, for example, to effect the filtration of a sample in the form of a suspension or to retain heavy compounds. The columns may be flushed separately; for example, in a first phase, the precolumn may alone be flushed, with or without recycling, by the sample containing dilute compounds, in order to retain same, the column being traversed by the vector or carrier fluid, and, in a second phase, the precolumn and the column are traversed in series in order to elute the compounds retained in the precolumn and to inject them into the separation column. The precolumn and the column may also be flushed separately when it is desired to eliminate or elute from the precolumn the products retained therein, such as, for example, heavy compounds, or products in suspension in the samples having been filtered; the precolumn is then flushed from bottom to top, the separation column being flushed by the flow of the vector liquid.

Thus, so that the precolumn and the column may be traversed in series or separately and that there will be no false or incorrect moves during the establishment of the different connections, the precolumn and the column are connected with each other and with the different fluid conduits by means of any suitable valves and capillary tubes.

The immediately aforesaid means to establish the different connections has the disadvantages of being complicated (valves, joints, etc.) and of introducing appreciable loss of precolumn efficiency due to the inevitable dead spaces in the connections between the outlet of the precolumn and the inlet of the separation column.

Generally compare U.S. Pat. No. 3,592,046, Cantwell, *Analytical Chemistry*, 48, No. 13, pp. 1854–1859 (Nov. 1976), French Pat. No. 1,269,160, and German Auslegeschrift No. 26 55 387.

SUMMARY OF THE INVENTION

Accordingly, a major object of the present invention is the provision of an improved device for a precolumn/column chromatography apparatus devoid of those disadvantages and drawbacks to date characterizing the state of the art, and one which does not entail any loss in column efficiency.

Briefly, the subject precolumn/column chromatography device, well adapted for liquid chromatography, is characterized in that it comprises both the support surfaces for a precolumn outlet and a column inlet and the means for connecting the inlet of the column and the outlet of the precolumn with each other, or with the fluid inlet and/or outlet means, in and/or from the said device.

In the description which follows, reference will be made, when necessary, to the direction of flow of the sample in the precolumn and in the column during the analysis.

Thus, from top to bottom consistent with the direction of flow of the sample, the ends of the precolumn shall be designated as the "inlet of the precolumn" and the "outlet of the precolumn" and the ends of the columns shall correspondingly be designated the "inlet of the column" and the "outlet of the column".

The device according to the present invention, more particularly, comprises:

(i) A body member provided with support surfaces for a column inlet and a precolumn outlet, said body member containing an aperture, said aperture being particularly connected with the outlet of the precolumn, the inlet of the column, with means for the inlet and/or outlet of the fluid, consisting of a plurality of conduits located in said body and opening into the said aperture through appropriate orifices or openings; and (ii) A stopper placed in said aperture and containing means to connect the inlet of the column and the outlet of the precolumn with each other, or with fluid inlet and/or outlet means, and/or an inlet means with an outlet means.

Also in the description which follows, "fluid inlet and/or outlet means" does not define, on the one hand, the nature of the fluid and, on the other, the direction of flow of the fluid in the conduits located in the body proper of the device; the direction of flow and the nature of the fluid depend essentially on the analytical problem requiring the combination of a column and a precolumn with the aid of the device according to the invention, as will become apparent from said description which follows.

In one embodiment of the invention, the stopper is essentially cylindrical and of rotating type, the connections being obtained by the rotation of the said stopper.

According to this particular embodiment, the connecting means borne by the said stopper consist of an essentially diametrical conduit and a plurality of conduits or grooves located on the external surface of the said stopper, said grooves, said conduit and the orifices of the fluid inlet and/or outlet means in the said recess being located essentially in the same plane perpendicular to the axis of the stopper.

According to another embodiment of the device according to the invention, the stopper is of piston type, with the connections being established by the translation and rotation of the said stopper.

According to yet another embodiment of the invention, the connecting means borne by the stopper may consist of essentially diametrical conduits spacedly arranged in the angular and longitudinal directions according to the axis of the said stopper, and of grooves according to the generatrices of the said stopper.

According to yet another embodiment, the connecting means borne by the said stopper may also consist of a plurality of conduits and an internal cavity with respect to the stopper.

Thus, according to this particular embodiment, the connecting means borne by the said stopper comprise:

(i) Two conduits in the shape of a V located in a first plane perpendicular to the axis of the stopper, the angle of the V being greater than 90°, the said two conduits opening onto the surface of the stopper through four orifices offset with respect to each other by 90°;

(ii) A cavity located inside the stopper and communicating with the outside of said stopper by means of two passageways located in a plane containing the axis of the stopper and opening onto the external surface of said stopper by means of two orifices, the said two orifices and one of the orifices of the V-shaped conduits being located on the same generatrix of the stopper; and (iii) An essentially diametrical conduit defined by a tube passing through said cavity located in a second plane perpendicular to the axis of the stopper and containing one of the passageways effecting the communication between said cavity and the outside of the stopper, said conduit being perpendicular to the plane containing said two passages.

The device to operably join, or interconnect, a column and a precolumn according to the invention may be such that the stopper comprises means for the control of the rotation and/or the translation of said stopper.

Advantageously, the means to control the rotation and/or the translation of the stopper and the body member of the subject device comprises means to visualize the connections established.

Generally, the device object of the invention is provided with means for securing the column and applying its inlet against the support surface of the body member. The device may also present means for securing the precolumn and applying its outlet against the support surface of the body member.

Generally, the device that is the object of the invention is such that the means to secure the column and the means to secure the precolumn consist of threaded cylindrical zones.

The column and/or the precolumn may be secured to the device according to the invention, for example, by means of a coupling operating by securing the column and/or the precolumn with a collar or a collar combined with a complementary collar.

Preferably, the column and/or the precolumn may be secured to the device that is the object of the invention by the application of a compressive force essentially axial with respect to the axis of the column, or of the precolumn with the aid of a device securing the column to a support, such as that described in U.S. Pat. No. 4,162,977.

Optionally, the device according to the invention may further comprise means for the injection of at least one standard.

Such means to inject at least one standard may consist of a piston valve, for example.

Optionally, the device according to the invention may be such that the body member of said device is defined by an assembly or array of blocks made integral by an appropriate means.

Thus, the device according to the invention may comprise, from top to bottom in the direction of the flow of the sample:

(i) A first block provided with support surface for a precolumn outlet;

(ii) A second block comprising means to connect the inlet of the column and the outlet of the precolumn with each other, or with fluid inlet and/or outlet means into and/or out of said device; and (iii) A third block provided with support surface for a column inlet.

Optionally, a block comprising means to introduce a standard is situated between the second and the third block.

Preferably, a gasket is placed between any two adjacent blocks; advantageously, said gasket is fabricated from polytetrafluoroethylene.

The device to operably combine a column with a precolumn that is the object of this invention is particularly suitable for use in the construction of an automatic laboratory or industrial chromatograph.

DETAILED DESCRIPTION OF THE INVENTION

Figure 1:
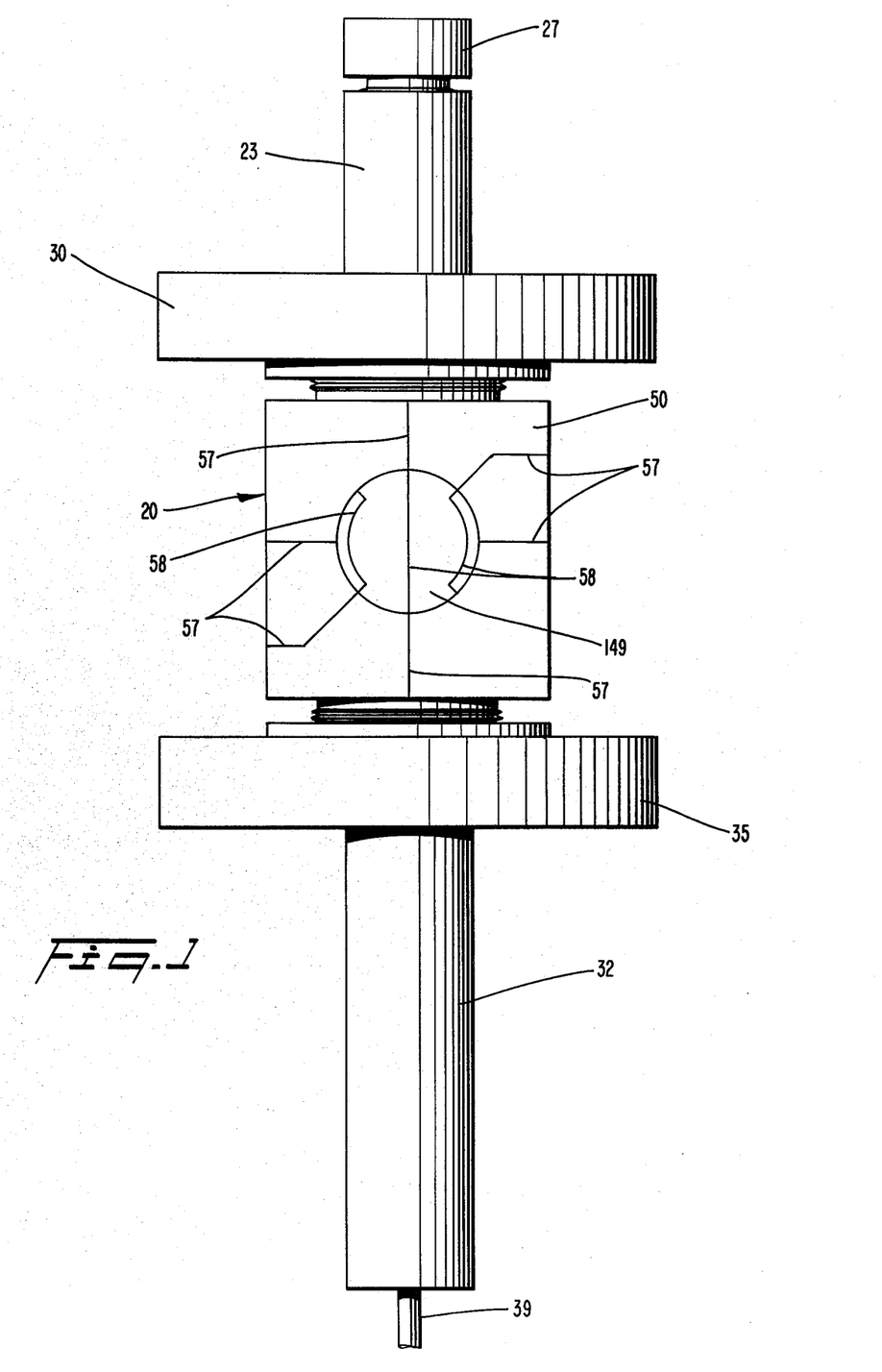
FIG. 1 is a plan view of one embodiment of the device for a precolumn/column chromatograph according to the present invention.
Figure 2:
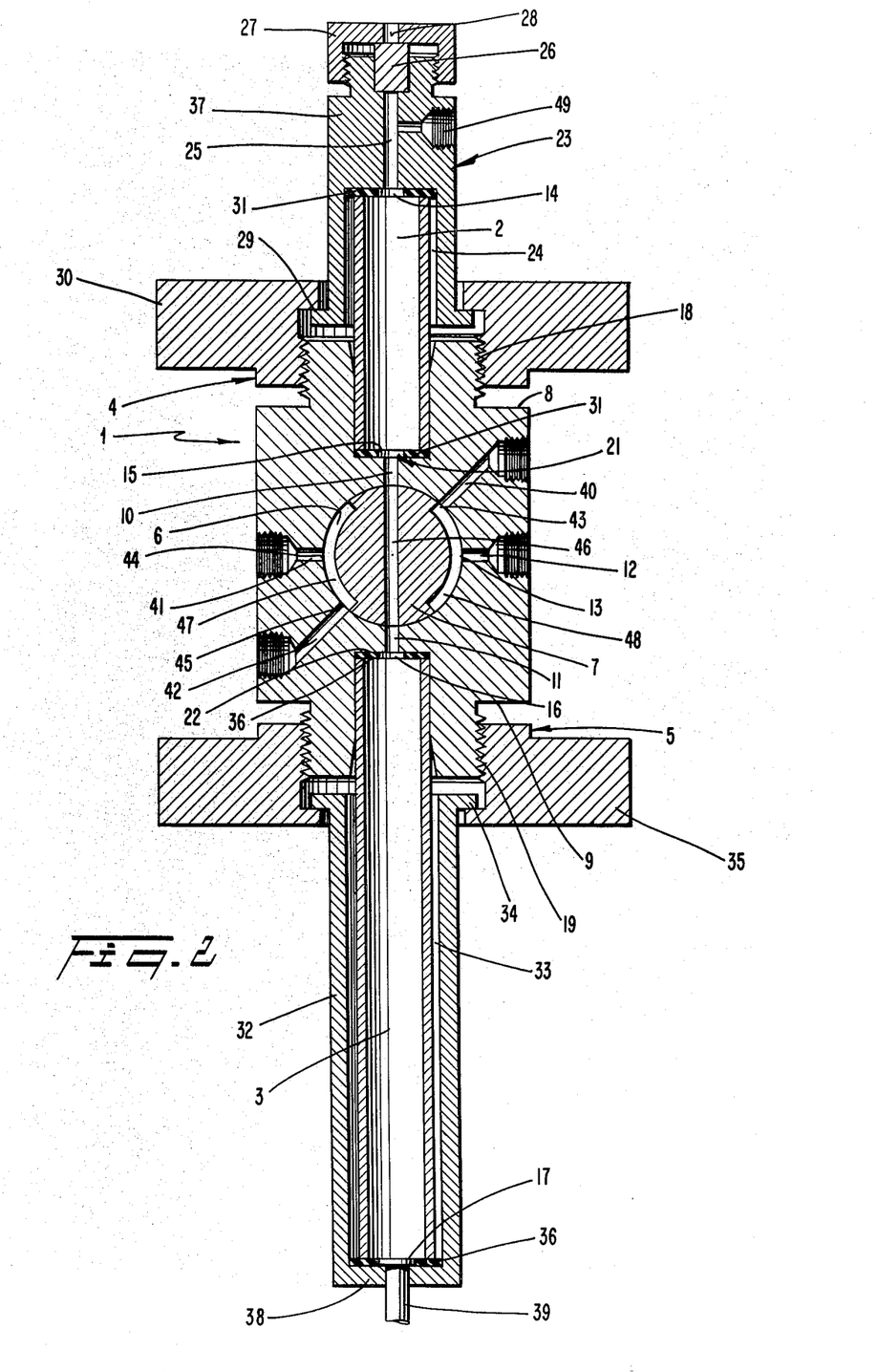
FIG. 2 is a cross-sectional view of the device illustrated in FIG. 1, on a plane perpendicular to the axis of stopper and containing the longitudinal axes of the column and precolumn.

More particularly according to this invention, and specifically referring to that embodiment illustrated in the accompanying FIGS. 1 and 2, a device 1 is shown which enables operably connecting a precolumn 2 with an analytical column 3 in a chromatography apparatus, the device comprising a body member 20 provided with support surfaces 21, 22 for a column 3 inlet 16 and a precolumn 2 outlet 15, and including an essentially cylindrical aperture 6, wherein is placed a stopper 7 of rotating type, together comprising the means to operably connect the inlet of the column with the outlet of the precolumn, either with each other or with fluid inlet and/or outlet means, and/or an inlet conduit and an outlet conduit.

From top to bottom in the direction of flow of the sample, the ends of the precolumn 2 will be designated as the precolumn inlet 14 and the precolumn outlet 15 and the ends of the column 3 are designated as the column inlet 16 and the column outlet 17.

The body member 20 of the subject device in the particular embodiment shown in FIG. 1 is essentially parallelepipedic in shape; it comprises two opposing face surfaces 8 and 9, with the means 4 for securing the precolumn 2 and the means 5 for securing the column 3 consisting of the threaded areas 18 and 19.

Preferably, in the manner shown, the precolumn 2 and the column 3 are secured to the device 1, which is the object of the invention, by the application of a compressive force essentially along the axis of the precolumn 2 and the column 3, applying the precolumn outlet 15 against the support surface 21 and the column inlet 16 against the support surface 22, said support surfaces 21 and 22 being on the body 20 for this purpose.

The precolumn 2 is secured to the device 1 by a compressive force applied via a precolumn holder 23 having an essentially cylindrical cavity 24 which engages the precolumn 2, said cavity 24 being closed at one end 37 and provided at its other end with an external annular rim or flange 29. A nut 30 in the configuration of a disk connects the annular rim 29 of the precolumn holder 23 with the cylindrical threaded zone 18 of the body member 20 according to the invention. Gaskets 31 are placed at each end of the precolumn 2, between said precolumn 2 and on the one hand, the precolumn holder 23, and on the other, the support surface 21 of the body member 20.

A conduit 25 serves to inject the sample into the precolumn inlet 14, for example, by means of a syringe injected through a septum 26, maintained by a plug 27 screwed onto the precolumn holder 23 and provided with an orifice 28 for the passage of the syringe needle.

The conduit 25 also communicates with at least one conduit 49, preferably threaded in the vicinity of the outside of the precolumn holder 23 for the easy application of a fitting thereto a fluid feed line. The conduit or conduits 49 may be closed off at any time by means of any suitable plug(s).

Optionally, the sample may be injected into the inlet 14 of the precolumn 2 by a valve means similar to that described in U.S. Pat. No. 4,168,235, the same being borne by the precolumn holder 23 and operably disposed on the conduit 25 upstream from the inlet 14 of the precolumn 2. The precolumn holder 23 in this embodiment does not include any laterally placed conduits 49, while that portion of the conduit 25 located toward the outside of the precolumn holder is threaded to allow for the application of a fitting for a fluid feed tube; it replaces the conduit 49.

A piston valve of this type shall be described hereinafter in the description of a second embodiment of the device according to the invention.

The column 3 is secured to the device 1 by a compressive force applied by means of a column holder 32 having an essentially cylindrical internal cavity 33 wherein the column 3 is engaged, said cavity 33 being sealed at one end by a wall member 38 and is provided at its other end with an external, annular rim or flange 34. A nut 35 in disk form secures the annular rim 34 of the column holder 32 to the threaded cylindrical zone 19 of the device according to the invention. The gaskets 36 are placed at each end of the column 3 between said column and, on one hand, the column holder 32 and, on the other, the support surface 22 of the body member 20 of the subject device.

The wall member 38 of the column holder 32 is provided with an aperture, permitting outlet of the outlet tube 39 to the detector.

Such means for the securing of the column and the precolumn are described in U.S. Pat. No. 4,162,977.

The central aperture 6 located in the body member 20 is connected, on the one hand, by means of the conduit or passageway 10 with the outlet 15 of the precolumn 2 and, on the other, by means of the conduit or passageway 11 with the inlet 16 of the column 3.

The aperture 6 is also connected with the fluid inlet means by means of a conduit or passageway 12 opening into the aperture 6 via orifice 13. The conduit 12 is typically utilized for the introduction of the vector fluid.

The aperture 6 is further connected with the fluid inlet and/or the fluid outlet means consisting of the conduits 40, 41 and 42 opening into the aperture 6 through the orifices 43, 44 and 45.

The conduits 40, 41 and 42 are preferably threaded in the vicinity of the outside of the body member 20 for the easy application thereto of fittings for the capillary, fluid tubes.

The rotating stopper 7 placed in the aperture 6 is essentially cylindrical and the fluid delivery means included within same consist, on the one hand, of an essentially diametrical conduit 46 and, on the other hand, by two grooves 47 and 48 located on the external surface of the stopper 7.

According to this particular embodiment of the invention, the conduit 46, the grooves 47 and 48, the conduits 10 and 11, the conduits 40, 41 and 42 and the conduit 12 have the sectioning plane of FIG. 1 as their plane of symmetry. The grooves 47 and 48 are further such that they enable connection of the conduits 12 and 40, 11 and 12, 10 and 41, by means of the rotation of the stopper 7.

Preferably, the aperture 6 is provided with a coating or lining of polytetrafluoroethylene, a material which provides both smooth sliding of the stopper in the aperture 6 and satisfactory sealing merely by the contact between the external surface of the stopper 7 and the internal surface of the aperture 6. Furthermore, polyfluoroethylene is highly inert to chemical substances and has good strength at elevated temperatures.

The stopper 7 comprises means to control its rotation, per the illustrated embodiment, such control means consisting of a knob in the form of a disk carried on the axis of the stopper 7. The face 50 of the body member 20, in front whereof the knob 149 is placed, and the knob itself, have means to display the various connections established. These means may consist of markings inscribed in the face surface 50 and in the knob. The markings 57 inscribed into the face surface 50 visualize the conduits 10, 11, 12, 41, 42 and 43 located within the body member 20, while the markings 58 inscribed into the knob itself visualize the conduit 46 and the grooves 47 and 48 of the stopper 7.

A second embodiment of the device to combine a precolumn with a column object of the invention is illustrated in the FIGS. 3 to 7.

In this second embodiment of the invention, not all of the elements constituting same and already present and described in the apparatus according to the first mode of embodiment, will here be recited in detail; such elements are noted with the same reference numerals.

Figure 3:
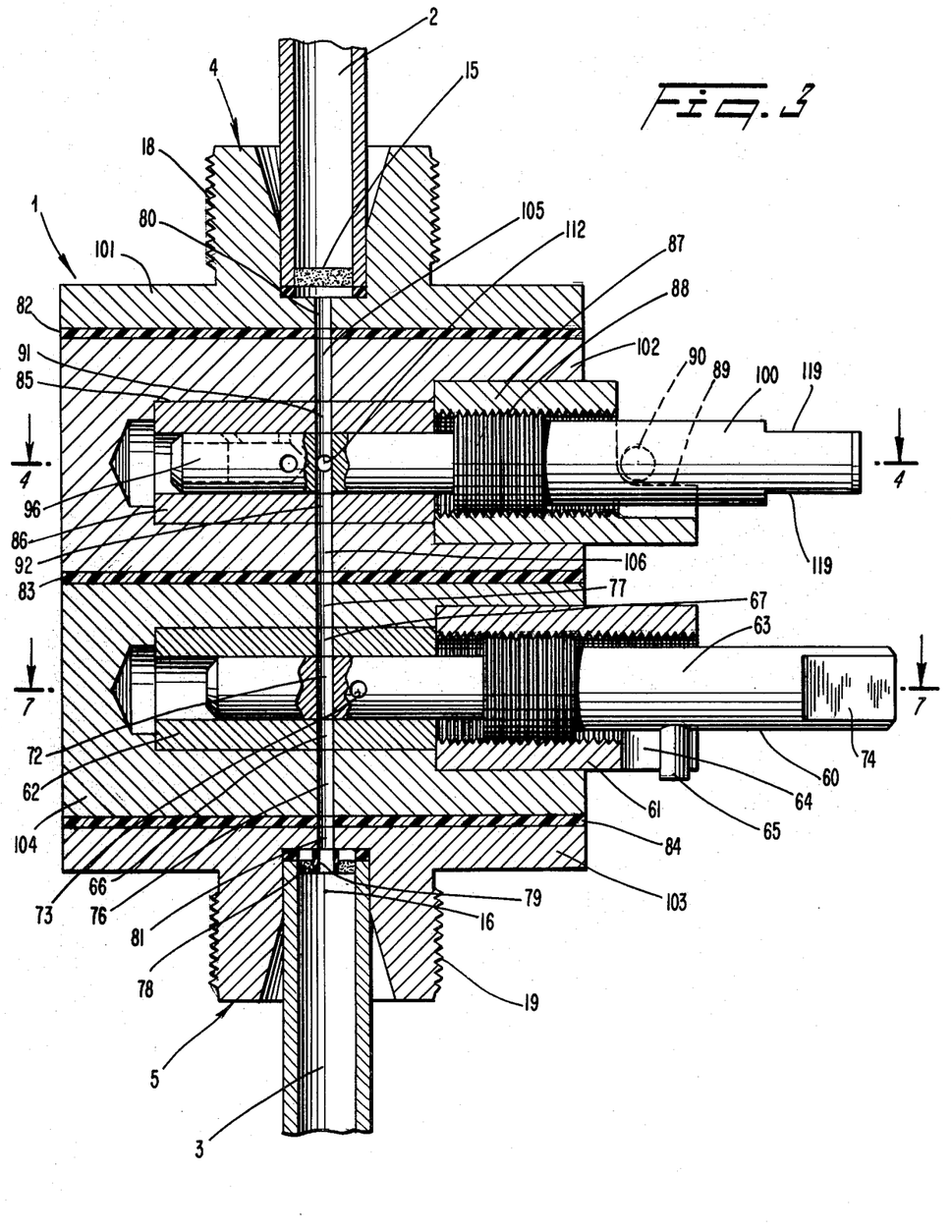
FIG. 3 is a cross-sectional view along the plane III—III (FIG. 4) of a second embodiment of the device for a precolumn/column chromatograph according to this invention, and including means for the injection of a standard.

And per this second embodiment of the invention, the body member of the device consists of an assembly of blocks secured together by any appropriate means.

Thus, the device consists, from top to bottom in the direction of the flow of the sample, of the four blocks 101, 102, 104 and 103.

The first block 101 contains fastening means 4 for the precolumn 2, and conduit 80 in communicating relationship with the outlet 15 of said precolumn 2.

The second block 102 comprises means for joining the inlet of the column with the outlet of the precolumn, either to each other or to inlet and/or outlet means for the fluid within and/or without said device [the block 102 and said connecting means shall be described hereinafter in more greater detail].

The third block 103 contains fastening means 5 for the column 3 and a conduit 81 in communicating relationship with the inlet 16 of the column 3. The conduit 81 advantageously is extended by means of hollow needle 79, which is, for example, welded to the block 103.

The hollow needle 79 is such that it penetrates through the porous wall 78 located at the inlet 16 of the column 3 at its center, i.e., axially with respect to the column 3. The length of the hollow needle 79 is selected such that said hollow needle 79 opens just at the interface between the porous wall 78 and the packing material of the column 3.

The fourth block 104, placed between the block 102 and the block 103, contains means to introduce a standard [the block 104 and the means to introduce the standard shall also be described hereinafter in more greater detail].

The four blocks 101, 102, 103 and 104, the assembly thereof constituting the device according to the invention, may be fastened together by means of screws, but a system of clamps or of springs may also be used.

Preferably, a gasket is placed between two adjacent blocks, said gaskets being provided with appropriate orifices for the passage of fluids.

Thus, the device shown in FIG. 3 comprises a gasket 82 placed between the first block 101 and the second block 102, a gasket 83 placed between the second block 102 and the third block 103 and a gasket 84 placed between the third block 104 and the fourth block 104.

Advantageously, the gaskets are fabricated from polytetrafluoroethylene.

The device shown in FIG. 3 consists of an assembly of blocks having flat opposing face surfaces, but an embodiment containing opposing faces that are not flat does not exceed the scope of the invention. In fact, one of the faces may bear at least two lateral rims or flanges corresponding to at least two lateral channels or depressions on the other face surface. This embodiment facilitates the positioning of the blocks during assembly of the device.

The fastening means 4 of the precolumn 2 carried by the block 101, and the fastening means 5 of the column 3 carried by the block 103, are similar to those described hereinabove in the description of the first embodiment according to the invention.

Block 102 bearing the fastening means, contains an aperture 85 wherein a body member 86 is placed, said body member consisting of a hollow cylinder to receive a piston type stopper 100, connections being established by the translation and rotation of said stopper.

The stopper 100 and the body member 86 are maintained in place with the aid of a support 87 of a generally cylindrical shape, fitted into an appropriate cavity formed in the block 102. The internal surface of the body 86 is provided at least in part with threading 88 cooperating with a corresponding threading borne by the stopper 100, said threadings making possible the displacement of the stopper 100 by translation and rotation. The wall of the support 87 contains a cutout 89 defined on one side by two planes containing the axis of the cylinder and enclosing among themselves an angle of approximately 90° [in view of the diameter of the lug 90 described hereinafter] and, on the other hand, by a plane perpendicular to the axis of the cylinder.

Preferably, the body 86 is fabricated from polytetrafluoroethylene, a material providing both easy sliding of the stopper 100 in the body 86 and satisfactory sealing merely by the contact between the external surface of the stopper 100 and the inner surface of the body 86, while being inert to chemicals and having good high temperature strength.

Figure 4:
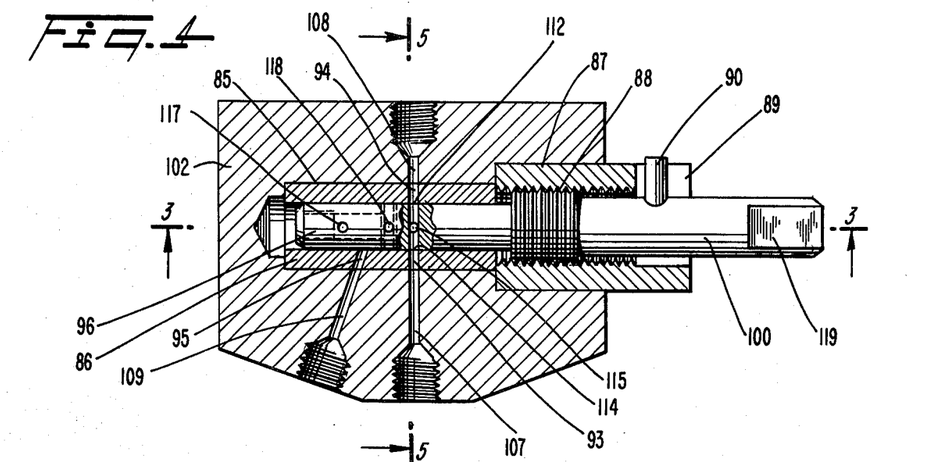
FIG. 4 is a cross-sectional view along the plane IV—IV of the device as illustrated in FIG. 3.

The body member 86 comprises a set of four holes 91, 92, 93 and 94 located in a plane perpendicular to the axis of the stopper 100 containing the axis of the precolumn 2 and the column 3, said holes being angularly offset by 90° and two of same being located along the axises of the precolumn 2 and the column 3. The body member 86 also contains a hole 95 located in a plane containing the axis of the stopper 100 and the holes 93 and 94, but spaced apart longitudinally on the axis of the stopper 100 toward the end 96 of the latter.

The holes 91, 92, 93, 94 and 95 of the body 86 communicate respectively with the passageways 105, 106, 107, 108 and 109 of the block 102.

In now describing the different connections established, the holes 91, 92, 93, 94 and 95 shall not be specifically mentioned; same should be considered as integral parts of the passageways 105, 106, 107, 108 and 109.

The passageway 105 of the block 102 communicates by means of the conduit 80 with the outlet 15 of the precolumn 2. The passageway 106 of the block 102 communicates by means of holes, passages and conduits of the block 104 to be described hereinafter, and by means of the conduit 81 of the block 103 with the inlet 16 of the column 3. The passageways 107, 108 and 109 of the block 102 are connected with the fluid inlet and/or outlet means; preferably, these passageways are threaded in the vicinity of the outside area of the block 102 for the easy application of a coupling. The passageway 107 is generally provided for the inlet of the vector or carrier fluid.

The piston type stopper 100 placed within the body 86 has the general form of an elongated cylinder, same having along its length and from inside the body 86 to the exterior thereof, two zones, which define the connection zone toward the inside of the body and the control zone toward the exterior thereof.

The control zone contains both the means to fasten the stopper 100 to the body 86 and the control means.

The means to fasten the stopper 100 to the body 86 consist of a threaded area which cooperates with the internal threading 88 of the body 86.

The control means consist, on the one hand, of two flat surfaces 119 provided at the end of the stopper 100 and making it possible to easily grip said end during the manipulation of the stopper 100 and, on the other hand, of a lug 90 which moves in the cutout 89 of the support 87, said lug 90 abutting against the two planes containing the axis of the stopper 100 and limiting the cutout 89 for each position of the stopper 100.

The connecting zone comprises connecting means which, according to the present embodiment of the invention, consist of a plurality of internal conduits and an internal cavity in the stopper 100.

Thus, the stopper 100 has, in a first cross-sectional plane perpendicular to its axis, two V-shaped conduits 110 and 111, the angle of the tip of the V being greater than 90° such that there exists no communication between the two conduits. The V-shaped conduits 110 and 111 open onto the surface of the stopper 100 through four orifices, with the conduit 110 opening through the orifices 112 and 113, the conduit 111 opening through the orifices 114 and 115, the orifices 112, 113, 114 and 115 being offset by 90° with respect to each other (FIG. 5b).

Figure 5A:
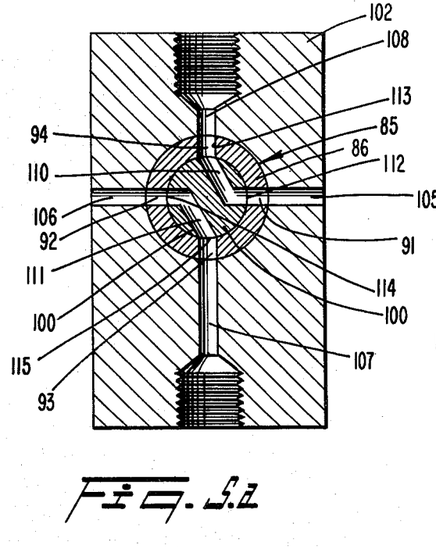
FIG. 5a is a cross-sectional view along the plane V—V of the block comprising the connecting means of the device shown in FIGS. 3 and 4, with the stopper being illustrated in a first position, and with FIG. 5b being a detailed view of said stopper.
Figure 5B:
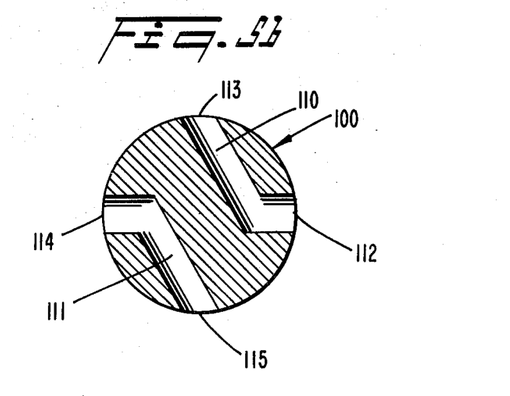

In the first position of the stopper 100 shown in FIG. 5a, the conduit in the form of a V 110 insures the connection between the passageways 105 and upstream of the latter, the outlet 15 of the precolumn 2 and the passageway 108 which is connected with the fluid inlet and/or outlet means. Simultaneously, the V-shaped conduit 111 insures the connection between the passageway 107 which may be the vector fluid inlet and the passageway 106 and downstream from the latter, with the inlet 16 of the column 3.

In another position of the stopper 100, obtained by rotating it by 90°, in the direction opposite to the trigonometric direction, the V-shaped conduit 110 insures the connection between the passageway 105 and upstream from the latter, the outlet 15 of the precolumn 2 and the passageway 107 which may be connected with the carrier fluid inlet. Simultaneously, the conduit in V form 111 assures the connection between the passageway 108 which is connected with the fluid inlet and/or outlet means—the passageway 108 may also be closed off by the provision of a plug—and the passageway 106 and downstream from the latter, with the inlet 16 of the column 3.

The connecting zone of the stopper 100 also contains a cavity 116, inside the stopper 100, which is communicating with the outside of the stopper by means of two passageways 117 and 118. The cavity 116 is longitudinally offset with respect to the axis of the stopper 100, toward the end 96 of the latter (the end opposite to the control zone); the cavity 116 is closed off tightly by a plug 99 secured, for example, by welding to the end 96 of the stopper 100.

The two passageways 117 and 118 are located on a plane containing the axis of the stopper 100; same open onto the surface of the stopper 100 respectively through the orifices 97 and 98, with the orifices 97 and 98 and the orifice 115 of the V-shaped conduit 111 being located on the same generatrix of the stopper 100 and the orifices 97 and 115 being located on either side of the orifice 98 and on either side thereof.

Figure 5C:
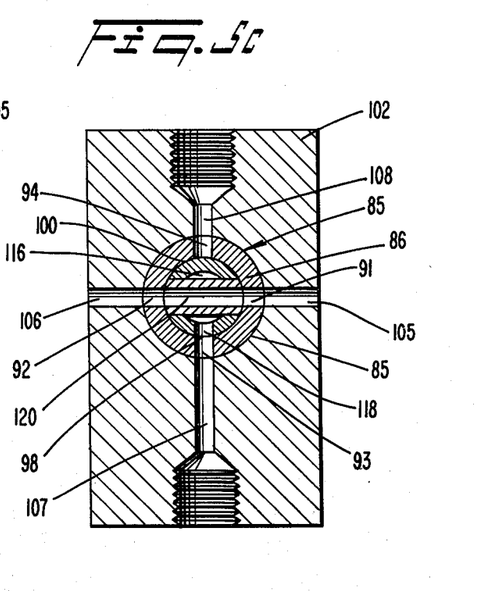
FIG. 5c is a cross-sectional view along the plane V—V of the block comprising the connecting means of the device shown in FIGS. 3 and 4, with the stopper being illustrated in a second position, and with FIG. 5d being a detailed view of said stopper.
Figure 5D:
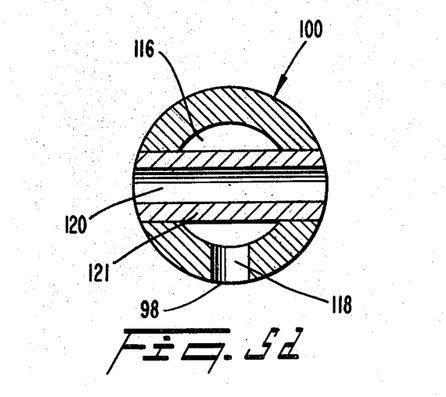
Figure 6:
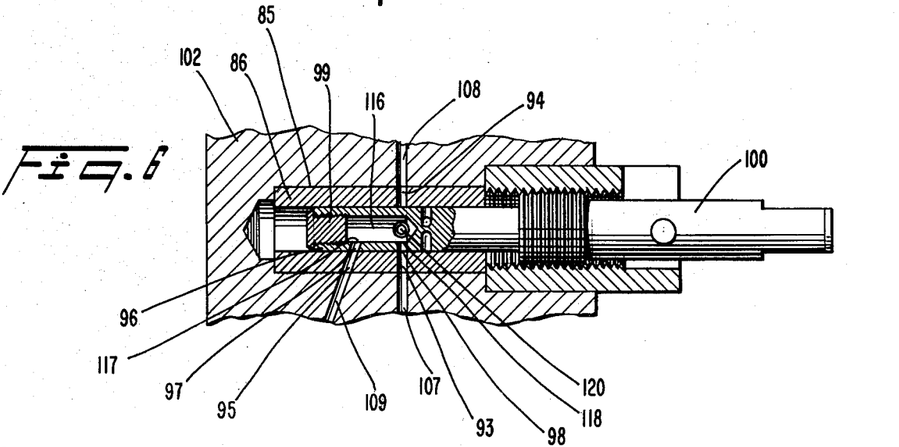
FIG. 6 is a partial cross-sectional view along the plane IV—IV of the block comprising the connecting means of the device shown in FIG. 3, with the stopper being in the second position as illustrated in FIG. 5c.

In the second position of the stopper 100 shown in FIG. 5c and FIG. 6, obtained by a 90° rotation of the stopper 100 in the direction opposite to the trigonometric direction and the longitudinal translation of a vector with a length equal to the distance between the orifices 98 and 115, the passageway 107 of the block 102, which serves as the vector fluid inlet, is connected through the passageway 118 of the cavity 116 and the passageway 117, with the passageway 109 which is then a fluid outlet means.

The connecting zone of the stopper 100 further contains an essentially diametrical conduit 120, defined by a tube 121, passing through the cavity 116 tightly fastened to the stopper 100, for example, by welding. The conduit 120 is located in a second plane perpendicular to the axis of the stopper and containing the passageway 118 connecting the cavity 116 to the outside of the stopper 100, the conduit 120 being perpendicular to the plane containing the passageways 117 and 118.

Thus, in the second position of the stopper 100, shown in FIG. 5c, the conduit 120 insures the connection between the passageway 105 of the block 102 and upstream from it the outlet 15 of the precolumn 2, and the passageway 106 of the block 102 and downstream therefrom, the inlet 16 of the column 3.

From the description of the block 102 according to the second embodiment of the device according to the invention, it will be seen that in the first position of the stopper 100, shown in FIG. 5a, the column 3 and the precolumn 2 may be traversed by a fluid independently of each other, and that in the second position of the stopper 100 shown in FIG. 5c, the precolumn 2 and the column 3 may be traversed in series by a fluid.

Figure 7:
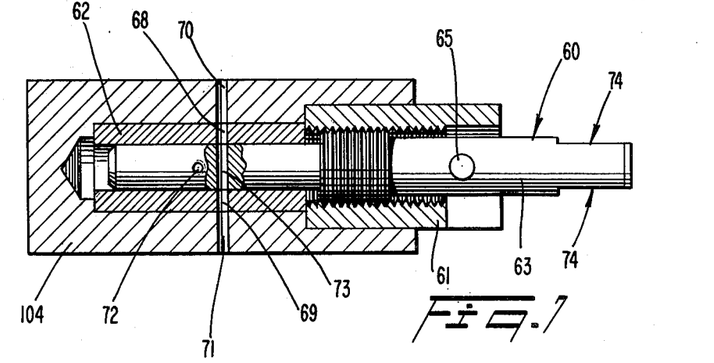
FIG. 7 is a cross-sectional view along the plane VII—VII of the device shown in FIG. 3, including means for injection of a standard.

The block 104 comprises means to introduce a standard, these means, according to the embodiment of the device of the invention shown in FIGS. 3 and 7, consisting of a piston-type valve 60 and enable introduction of at least one standard into the inlet 16 of the column 3.

The valve 60 effects the introduction of the standard downstream from the passageway 106 of the block 102 and from there to the inlet 16 of the column 3 by means of the conduit 81 of the block 103.

The valve 60 consists of a valve support 61, a cock-shell 62 and a piston 63.

The generally cylindrical valve support 61 is housed within an appropriate cavity formed in the block 104, its internal surface being provided, at least in part, with suitable threading. The wall of the support contains a cutout 64 defined on the one hand, by two planes containing the axis of the cylinder and describing among themselves an angle of approximately 90° in view of the diameter of the lug 65 described hereinafter and, on the other hand, by a plane perpendicular to the axis of the cylinder.

The cock-shell 62 of the valve 61 consists of a hollow cylinder placed in a cylindrical cavity of the block 104; same contains two sets of two diametrically opposed holes, offset longitudinally along the axis of the cock-shell and offset angularly, by an angle of approximately 90°, with respect to each other. The first set of holes 66 and 67 is such that the holes communicate with the passageways 76 and 77 of the block 104. The second set of holes 68 and 69 communicates with the feed channels 70 and 71 by the flow of the standard.

Preferably, the cock-shell 62 is fabricated of polytetrafluoroethylene, a material that provides both easy sliding of the piston 63 in the cock-shell 62 and satisfactory sealing merely by the contact between the external surface of the piston 63 and the inner surface of the cock-shell 62 and which is highly inert to chemical action.

The piston 63, placed inside the cock-shell 62, has the shape of an elongated cylinder; it has, over the length and from the inside to the outside of the block 104, two zones, which toward the inside of the block 104 is the feed and injection zone of the standard and toward the outside of the block 104, the control zone.

The feed and injection zone contains a passageway 72 and an aperture 73 for the standard. The passageway 72 and the aperture 73 are essentially diametrical and traverse the piston 63 from side to side. They are appreciably offset along the longitudinal axis of the piston 63 and offset angularly by an angle of approximately 90°. In a position of the piston 63 such as that shown in FIGS. 3 and 7, the passageway 72 insures communication between the holes 66 and 67, communicating with the passageways 76 and 77 of the block 104, the aperture 73 is then simultaneously in communication with the channels 70 and 71 for the feeding of the standard. The channel 70 is, preferably, threaded in the vicinity of the outside of the block 104 to make possible the easy application of a coupling. In the injection position of the piston 63, communication between the holes 66 and 67 is established by means of the aperture 73, with the passageway 72 then being neutralized, or avoided.

The translation of the piston 63 from the position shown in FIGS. 3 and 7, to the position permitting the injection of the standard, that position wherein the aperture 73 replaces the passageway 72, is effected by a translation movement on the axis of the piston for a distance equal to the longitudinal distance between the passageway 72 and the aperture 73, simultaneously with a rotating movement about this same axis by an angle equal to the angular offset existing between the passageway 72 and the aperture 73.

The control zone contains both the means to secure the piston 63 to the support 61 and the control means.

The means to secure the piston 63 to the support 61 consist of a threaded zone cooperating the inner threaded surface of the support 61.

The control means consist, on the one hand, of two flat surfaces 74 located at the end of the piston 63, said flat surfaces permitting the easy gripping of said end during the manipulation of the piston 63, and on the other, of a lug 65 moving in the cutout 64 of the support 61, the lug 65 abutting against the two planes containing the axis of the piston 63 and defining the cutout 64 for each position of the piston 63, either the passageway 72 or the aperture 73 being in communicating relationship with the holes 66 and 67 which in turn communicate with the passageways 76 and 77 of the block 104.

The position of the piston 63 such that the aperture 73 communicates with the passageways 76 and 77 of the block 104 by means of the holes 66 and 67, permits the injection of a standard into the inlet 16 of the column 3 via the conduit 81.

The focus of the invention features establishing precolumn/column connections by eliminating to the maximum possible extent the loss in efficiency of the separation column due to dead volumes. It should be noted that the subject device permits attainment of this objective.

In actual fact, in the resolution of various analytical problems, it is often necessary to flush in series the precolumn and the column, for example, in order to elute therein the compounds retained by the precolumn or the sample filtered by the precolumn. Thus, with the device according to the invention, the outlet 15 of the precolumn 2 and the inlet 16 of the column 3 are directly connected, without any change in direction of flow and without a dead volume, by means of the passageway 80 of the block 101, the passageway 105 of the block 102, the conduit 120 of the stopper 100, and optionally, if a standard is being injected, the passageways 77, 72 and 76 of the means to inject the standard, and the passageway 81.

The device to operably combine a precolumn and a column in liquid phase chromatography that is the object of the invention, makes it possible to readily resolve analytical problems posed by the analysis of samples containing heavy compounds, or highly dilute compounds, or the analysis of suspensions.

Figure 8A:
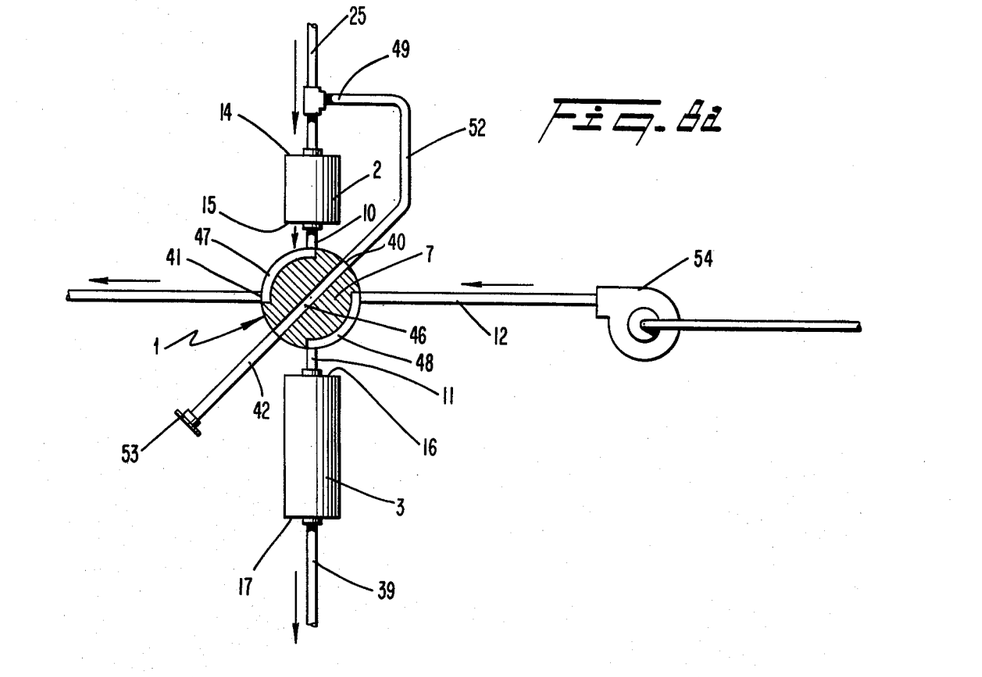
FIGS. 8a and 8b are diagrammatic/schematic views of two phases of the solution of a first analytical problem utilizing the device according to the invention, in a first embodiment thereof.
Figure 8B:
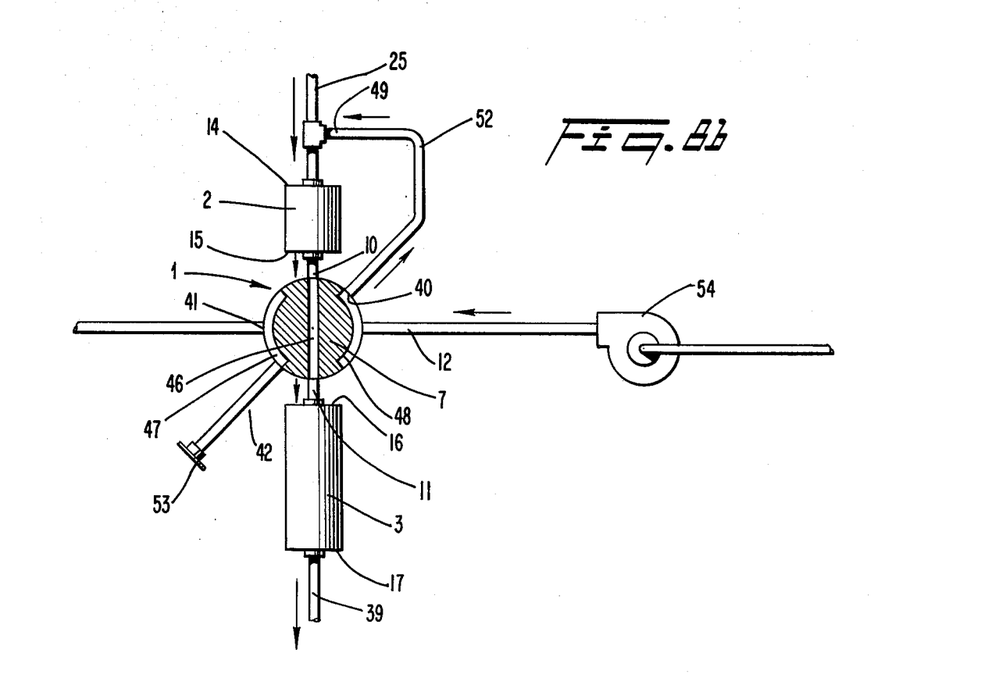
Figure 9A:
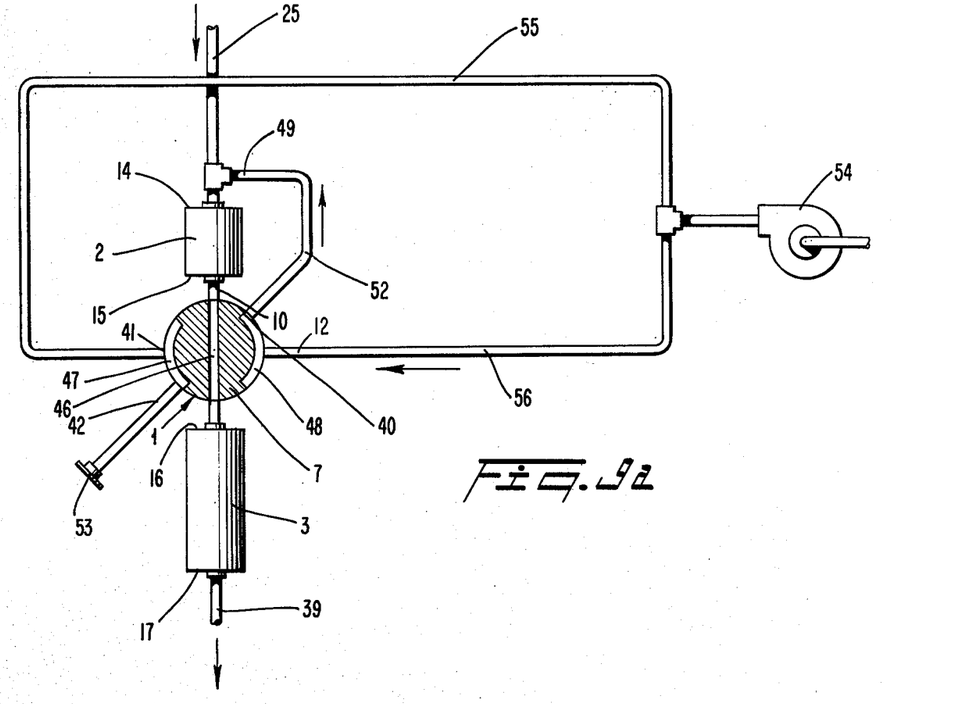
FIGS. 9a and 9b are diagrammatic/schematic views of two phases of the solution of a second analytical problem utilizing the device according to the invention, in a second embodiment thereof.
Figure 9B:
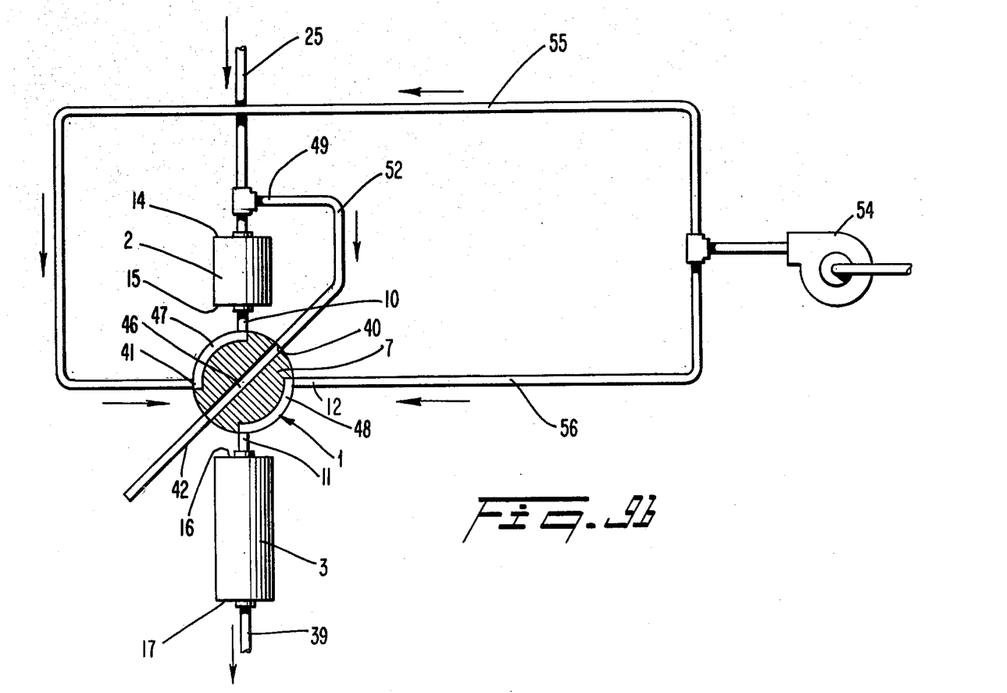

Exemplary of this, FIGS. 8 and 9 schematically show the use of the apparatus according to the invention, in the first embodiment thereof, in the analysis of highly dilute samples (FIGS. 8a and 8b) and in the analysis of suspensions (FIGS. 9a and 9b).

In the analysis of highly dilute samples, in a first operating phase, only the precolumn is flushed with the sample in order to retain the compounds to be identified, while the column is flushed with the vector or carrier fluid, while in a second phase, the precolumn and the column are successively in order to elute, in the separation column, the compounds that had been retained in the precolumn.

Thus, in the first phase (FIG. 8a), the stopper 7 of the device according to the invention is disposed such that:
 (i) The outlet 15 of the precolumn 2 is operably connected with the conduit 41 by means of the conduit 10 and the groove 47 of the stopper 7; and
 (ii) The inlet 16 of the column 3 is operably connected with the conduit 12 for the introduction of the vector fluid by means of the conduit 11 and the groove 48 of the stopper 7.

Further, the conduit 40 of the body member 20 is connected by a tube 52 with the conduit 49 of the precolumn holder 23.

The conduit 42 is closed off by means of the plug 53.

During this first operating phase, the dilute sample is injected or fed continuously into the inlet 14 of the precolumn 2, through which it flows. The compounds to be identified are retained by the precolumn 2, the depleted sample leaves the precolumn 2 through the outlet 15 and is removed by means of the conduit 10, the groove 47, the conduit 41. Optionally, if necessary, recycling of the depleted sample may be established by connecting with the aid of a tube the conduit 41 with the conduit 25, by means of a conduit similar to the conduit 49, until the sample is exhausted of compounds to be identified.

Simultaneously, the carrier or vector liquid is charged, by means of a pump 54 by means of the conduit 12, the groove 48 and the conduit 11, to the inlet 16 of the column 3.

In the second phase (FIG. 8b), the stopper 7 of the device according to the invention is disposed such that:
 (i) The outlet 15 of the precolumn 2 is operably connected with the inlet 16 of the column 3 by means of the conduit 46 of the stopper 7; and
 (ii) The vector or carrier fluid feed conduit 12 is operably connected with the inlet 14 of the precolumn 2 by means of the groove 48 of the stopper 7, the conduit 40, the conduit 49 and the conduit 25.

During this second phase of operation, the vector fluid is fed, with the aid of the pump 54, by means of the conduit 12, the groove 48, the conduit 40, the tube 52, the conduit 49 and the conduit 25, to the inlet 14 of the precolumn 2, through which it flows while eluting the compounds of the sample retained therein, toward the inlet 16 of the column 3 for separation, by means of the conduit 10, the conduit 46 of the stopper 7 and the conduit 11. At the outlet 17 of the column 3, the vector fluid carries the eluate through the conduit 39 to the detector.

To analyze samples in the form of a dispersion, in the first operating phase, the precolumn and the column are traversed in series, with the precolumn effecting the filtering of the sample, and in a second phase, same are traversed in the inverse direction to clean the precolumn and to effect the elution of the components of the sample retained by the column and to convey such components to the detector.

Prior to the analysis in the form of a suspension.
(i) The vector fluid feed conduit 12 and the conduit 41 are both connected by the tubes 55 and 56 with the pump 54 for feeding the vector fluid; and
(ii) The conduit 40 of the body member 20 is connected by means of a tube 52 to the conduit 49 of the precolumn holder 23.

Thus, in the first phase (FIG. 9a), the stopper 7 of the device according to the invention is located such that:
(i) The inlet 14 of the precolumn 2 is connected with the conduit 12 to introduce the vector fluid by means of the groove 48 of the stopper 7, the conduit 40, the tube 52, the conduit 49 and the conduit 25; and
(ii) The outlet 15 of the precolumn 2 is connected with the inlet 16 of the column 3 by means of the conduit 10, the conduit 46 of the stopper 7 and the conduit 11.

The conduit 42 is closed off by the plug 53.

During this first operating phase, the sample is injected in the inlet 14 of the precolumn 2 by means of the conduit 25; it is entrained by the vector fluid supplied by the conduit 49, in the conduit 25. The sample flows through the precolumn 2 where it is filtered, exits the precolumn 2 through the outlet 15, is transported through the conduit 10, the conduit 46 of the stopper 7, the conduit 11, to the inlet 16 of the column 3. At the outlet 17 of the column 3, the vector fluid transports the eluate through the conduit 39 to the detector.

In the second phase (FIG. 9b), the stopper 7 of the device according to the invention is disposed such that:
(i) The inlet 16 of the column 3 is connected with the conduit 12 for the supply of the vector fluid, by means of the conduit 11 and the groove 48 of the stopper 7; and
(ii) The outlet 15 of the precolumn 2 is connect by means of the conduit 41, the groove 47 of the stopper 7, the conduit 41 to the pump 54.
(iii) The conduit 42 is connected with the conduit 40 by means of the conduit 46 of the stopper 7 and from there with the tube 52, the conduits 49 and 25 of the precolumn holder 23, and from there, with the inlet 14 of the precolumn 2.

The conduit 42 is open, the plug 53 having been removed.

During this second operating phase, the vector fluid continues the elution of the components retained in the column 3, while in the precolumn 2 the vector fluid flows in the direction opposite to its direction of flow during the first operating phase and cleans the precolumn, the contaminated vector fluid being moved outward by means of the conduits 25 and 49 of the precolumn holder 23, the tube 52, the conduit 40, the conduit 46 of the stopper 7, and the conduit 42.

The resolution, or solving, of two analytical problems by utilizing the device consistent herewith has been described hereinabove as an example only and it is of course within the capability of those skilled in the art to use said device to solve other analytical problems requiring the combination of two columns.

Thus, a person skilled in the art may use the device according to the invention for the analysis of samples containing heavy compounds which are not undesirable. In this case, in a first operating phase, the column and the precolumn are traversed in series by the sample, the heavy compounds having been retained by the precolumn, and in a second operating phase the precolumn and the column are separately traversed by the vector liquid, the heavy compounds retained by the precolumn being eluted to a first detector, the other compounds retained by the column being eluted to a second detector.

Even though there has been described hereinabove a device wherein the connecting means are borne by an essentially cylindrical stopper of rotating or piston type, it is also within the capability of a person skilled in the art to develop other connecting means, such as, for example, a piston type stopper with its connecting means consisting of essentially diametrical conduits offset angularly and longitudinally with respect to the axis of the stopper, the conduits being associated with grooves on the generatrices of the stopper.

The device to combine a precolumn and a column according to the invention is of particular interest in the development of an automatic industrial chromatograph, the translation and/or the rotation of the stopper being controlled by programming or a servo mechanism.

The device according to the invention, thus, has numerous advantages.

In effect, the device according to the invention makes it possible to connect readily, and at will, the inlet of the column and the outlet of the precolumn with each other and with the fluid inlet and/or outlet means within and/or without the device, with several connections being possible simultaneously. Furthermore, the establishment or the disengagement of these connections are effected only by controlling the stopper and do not require the mounting and/or disassembly of connecting tubes and/or the manipulation of a number of valves.

An important advantage of the device to combine a precolumn and a column that is the object of the present invention, is that it eliminates the loss of efficiency of the separation column due to the inevitable dead volumes formed by connections effected with the aid of capillary tubes and valves between the inlet of the column and the outlet of the precolumn, in the embodiments according to the prior art.

In addition, the actual use of the device according to the invention may easily be automated.

Even though the present text refers to the method of liquid phase chromatography, the device that is the object of the invention may be used to combine a precolumn and a column in gaseous phase chromatography and may be employed in the development of a gaseous phase chromatograph.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a fluid chromatography apparatus, a device for operably connecting a precolumn and a column, said device comprising a body member including support surfaces for a column inlet and a precolumn outlet and including a central aperture, first conduit means respectively extending from said aperture to said precolumn outlet and column inlet, and second conduit means extending from said aperture to a plurality of external fluid inlet and/or outlet means, and a stopper for said central aperture, said stopper comprising a passage for directly interconnecting said precolumn outlet with said column inlet by means of a substantially linear flow path, and passages for independently connecting each of said precolumn outlet and column inlet to individual ones of said external fluid inlet and/or outlet conduits.

2. The device as defined by claim 1, said stopper being essentially cylindrical and adapted for rotation within said central aperture, and said various connections adapted to be made by rotation of said stopper.

3. The device as defined by claim 2, said first conduit means comprising an essentially diametrical linear conduit, said stopper including orifice means for directing external fluid inlet and/or outlet to or from said precolumn outlet and column inlet.

4. The device as defined by claim 3, said conduit and orifice means being located in essentially the same plane, perpendicular to said stopper.

5. The device as defined by claim 1, said stopper being of piston type, and said various connections adapted to be made by translation and rotation of said stopper.

6. The device as defined by claim 5, said connecting means comprising said stopper comprising a plurality of essentially diametrical conduits offset both angularly and longitudinally with respect to the axis of said stopper, and respective grooves therefor, along the generatrices of said stopper.

7. The device as defined by claim 5, the connecting means borne by said stopper comprising a pair of V-shaped conduits located in a first plane perpendicular to the axis thereof, the angle of the V being greater than 90°, said conduits extending to four orifices opening onto the external surface of said stopper, said orifices being angularly offset at angles of about 90°, said stopper including an internal cavity communicating to the exterior thereof by two passageways situated in the same plane containing the axis of the stopper and extending to two orifices opening onto the external surface of said stopper, said two orifices and one of the orifices comprising said V-shaped conduit being located on the same generatrix of the stopper, and a tubular, essentially diametrical conduit extending through said internal cavity located in a second plane perpendicular to the axis of the stopper and containing one of the passageways connecting said cavity to the exterior of the stopper, said tubular conduit being perpendicular to the plane containing said passageways.

8. The device as defined by claims 1 or 7, wherein said stopper comprises means for controlling the rotation and/or translation of said stopper.

9. The device as defined by claim 8, wherein said body member and said control means further comprise means for visually displaying the connections established.

10. The device as defined by claim 1, said body member including means for securing the column thereto, with the column inlet being applied against a support surface thereof.

11. The device as defined by claim 10, comprising means for securing the precolumn thereto, with the precolumn outlet being applied against a support surface thereof.

12. The device as defined by claim 11, said means for securing the column and precolumn to the body member each comprising a cylindrical threaded zone.

13. The device as defined by claim 1, further comprising means for the injection therein of at least one standard.

14. The device as defined by claim 13, said injection means comprising a piston-type valve.

15. The device as defined by claim 1, wherein said body member comprises an integral assemblage of block elements.

16. The device as defined by claim 15, comprising, in the direction of flow of sample, a first block element comprising a support surface for the precolumn outlet thereto and a conduit in communicating relationship with said precolumn outlet, a second block element comprising means for interconnecting the column inlet with the precolumn outlet, and individually independently with fluid inlet and/or outlet means, either internally or externally, and a third block element comprising a support surface for the column inlet thereto and a conduit in communicating relationship with said column inlet.

17. The device as defined by claim 16 in which the first block element and the third block element comprise means for securing respectively a precolumn and a column.

18. The device as defined by claim 16, further comprising a fourth block element, located between said second and said third block elements, and said fourth block element comprising means for the injection of at least one standard.

19. The device as defined by claim 18, said gasket means being fabricated from polytetrafluoroethylene.

20. The device as defined by claim 16, comprising gasket means disposed between each two adjacent block elements.

* * * * *